(12) United States Patent
Buchanan

(10) Patent No.: US 7,722,667 B1
(45) Date of Patent: May 25, 2010

(54) TWO PIECE BIOPROSTHETIC HEART VALVE WITH MATCHING OUTER FRAME AND INNER VALVE

(75) Inventor: Eric S. Buchanan, Wyoming, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 0 days.

(21) Appl. No.: 09/572,827

(22) Filed: May 17, 2000

Related U.S. Application Data

(63) Continuation-in-part of application No. 09/203,169, filed on Dec. 1, 1998, now Pat. No. 6,074,418, which is a continuation-in-part of application No. 09/062,822, filed on Apr. 20, 1998, now Pat. No. 6,176,877.

(51) Int. Cl.
*A61F 2/24* (2006.01)
(52) U.S. Cl. ............................ 623/2.14; 623/2.38
(58) Field of Classification Search ......... 623/2.1–2.19, 623/2.38–2.42, 904, 910, 918, FOR. 101, 623/1.24, 1.26, 900, 902
See application file for complete search history.

(56) References Cited

U.S. PATENT DOCUMENTS

| | | | |
|---|---|---|---|
| 3,143,742 A | 8/1964 | Cromie | |
| 3,503,079 A | 3/1970 | Smith | |
| 3,546,710 A | 12/1970 | Shumakov et al. | |
| 3,574,865 A | 4/1971 | Hamaker | |
| 3,587,115 A | 6/1971 | Shiley | |
| 3,686,740 A | 8/1972 | Shiley | |
| 3,835,475 A * | 9/1974 | Child .................. | 623/2.23 |
| 4,078,268 A | 3/1978 | Possis | |
| 4,364,126 A | 12/1982 | Rosen et al. | |
| 4,612,011 A | 9/1986 | Kautzky | |
| 4,680,031 A | 7/1987 | Alonso | |
| 4,683,883 A | 8/1987 | Martin | |
| 4,705,516 A | 11/1987 | Barone et al. | |
| 4,865,600 A | 9/1989 | Carpentier et al. | |
| 4,892,541 A | 1/1990 | Alonso | |
| 4,994,073 A | 2/1991 | Green | |
| 5,032,128 A | 7/1991 | Alonso | |
| 5,035,709 A | 7/1991 | Wieting et al. | |
| 5,071,431 A | 12/1991 | Sauter et al. | |
| 5,163,954 A | 11/1992 | Curcio et al. | |
| 5,211,658 A | 5/1993 | Clouse | |
| 5,290,300 A | 3/1994 | Cosgrove et al. | |
| 5,354,330 A | 10/1994 | Hanson et al. | |
| 5,370,685 A | 12/1994 | Stevens | |
| 5,397,346 A | 3/1995 | Walker et al. | |

(Continued)

FOREIGN PATENT DOCUMENTS

DE         265 752 A3 *   3/1989     ........ 623/FOR. 101

(Continued)

*Primary Examiner*—David H. Willse
(74) *Attorney, Agent, or Firm*—Hallie A. Finucane; Westman, Champlin & Kelly, P.A.

(57) ABSTRACT

A bioprosthetic heart valve includes an outer frame configured to attach to a tissue annulus of a heart and an inner bioprosthetic valve having an exterior shape which substantially matches an interior shape of the outer frame. The exterior shape of the inner valve mates in substantial alignment with the interior shape of the outer frame. An outer frame-inner valve attachment mechanism is configured to couple the inner valve to the outer frame.

9 Claims, 17 Drawing Sheets

U.S. PATENT DOCUMENTS

| | | | |
|---|---|---|---|
| 5,411,552 A * | 5/1995 | Andersen et al. | 623/2.18 |
| 5,417,699 A | 5/1995 | Klein et al. | |
| 5,476,510 A | 12/1995 | Eberhardt et al. | |
| 5,489,298 A * | 2/1996 | Love et al. | 623/2.14 |
| 5,531,678 A | 7/1996 | Tomba et al. | |
| 5,562,729 A | 10/1996 | Purdy et al. | |
| 5,593,424 A | 1/1997 | Northrup, III | |
| 5,607,470 A | 3/1997 | Milo | |
| 5,697,382 A | 12/1997 | Love et al. | |
| 5,716,370 A | 2/1998 | Williamson, IV et al. | |
| 5,733,331 A | 3/1998 | Peredo | |
| 5,766,240 A | 6/1998 | Johnson | |
| 5,776,187 A | 7/1998 | Krueger et al. | |
| 5,776,188 A | 7/1998 | Shepherd et al. | |
| 5,810,848 A | 9/1998 | Hayhurst | |
| 5,843,164 A | 12/1998 | Frantzen et al. | |
| 5,855,597 A | 1/1999 | Jayaraman | |
| 5,855,601 A | 1/1999 | Bessler et al. | |
| 5,895,419 A | 4/1999 | Tweden et al. | |
| 5,935,163 A * | 8/1999 | Gabbay | 623/2.14 |
| 5,954,747 A | 9/1999 | Clark | |
| 5,984,959 A | 11/1999 | Robertson et al. | |
| 6,074,418 A | 6/2000 | Buchanan et al. | |
| 6,096,074 A | 8/2000 | Pedros | |
| 6,113,632 A | 9/2000 | Reif | |
| 6,143,025 A | 11/2000 | Stobie et al. | |
| 6,162,208 A | 12/2000 | Hipps | |
| 6,786,925 B1 | 9/2004 | Schoon et al. | |
| 2001/0044656 A1 * | 11/2001 | Williamson et al. | 623/2.11 |

FOREIGN PATENT DOCUMENTS

| | | | | |
|---|---|---|---|---|
| EP | 0 119 357 A1 | | 9/1984 | |
| EP | 0 544102 A1 | | 6/1993 | |
| EP | 0 850 607 A1 * | | 7/1998 | |
| GB | 1 600 506 | | 10/1981 | |
| GB | 2 136 533 A * | | 9/1984 | 623/FOR. 101 |
| RU | 1806696 A * | | 4/1993 | 623/FOR. 101 |
| WO | WO 87/05489 | | 9/1987 | |
| WO | WO-90/11738 | * | 10/1990 | 623/FOR. 101 |
| WO | WO 91/14408 | | 10/1991 | |
| WO | WO 91/17720 | | 11/1991 | |
| WO | WO-95/28899 A * | | 11/1995 | 623/FOR. 101 |
| WO | WO 96/03925 | | 2/1996 | |
| WO | WO 97/09948 | | 3/1997 | |
| WO | WO 97/30659 | | 8/1997 | |
| WO | WO 97/49357 | * | 12/1997 | 623/FOR. 101 |
| WO | WO 98/43556 | | 10/1998 | |

* cited by examiner

TWO PIECE BIOPROSTHETIC HEART VALVE WITH MATCHING OUTER FRAME AND INNER VALVE

CROSS-REFERENCE TO RELATED APPLICATION

This application is a continuation-in-part of application Ser. No. 09/203,169, filed Dec. 1, 1998, now U.S. Pat. No. 6,074,418, and entitled "DRIVER TOOL FOR HEART VALVE PROSTHESIS FASTENERS", which is a continuation-in-part of application Ser. No. 09/062,822, filed Apr. 20, 1998, now U.S. Pat. No. 6,176,877, and titled "TWO PIECE PROSTHETIC HEART VALVE."

FIELD OF THE INVENTION

The present invention relates to mechanical heart valve prostheses. More specifically, the invention relates to a driver tool for attaching and implanting heart valve prostheses.

BACKGROUND OF THE INVENTION

Implantable mechanical heart valves are used for replacement of defective valves in hearts of patients. One common method employs a sewing ring or suture cuff which is attached to and extends around the outer circumference of the mechanical valve orifice. The sewing cuff is made of a biocompatible fabric suitable for allowing a needle and suture to pass therethrough. The valves are typically sutured to a tissue annulus that is left when the surgeon removes the existing valve from the patient's heart. The sutures are tied snugly, thereby securing the valve to the heart.

Sewing cuffs are labor intensive, difficult to manufacture and may be difficult to secure to the valve orifice. Further, attaching the suture cuff to the tissue annulus is time consuming and cumbersome. The complexity of suturing requires a patient to be on cardiopulmonary bypass for a lengthy period. It is also desirable to provide a large lumen through the valve orifice relative to the overall valve diameter for blood flow. However, techniques for attaching the sewing cuff to the valve orifice typically require that the area of the valve lumen be reduced to accommodate an attachment mechanism. For example, the sewing cuff is typically retained between two rims of the valve orifice. One of the rims normally defines the outside diameter of the valve orifice and thus limits the size of the valve lumen.

Another technique for attaching heart valves uses a series of pins which pierce the tissue annulus of the heart. The pins are crimped or bent, thereby locking the valve to the heart tissue and preventing the valve from separating from the heart. This technique is described in U.S. Pat. Nos. 3,574,865 and 3,546,710. Another technique for attaching a prosthetic heart valve to the heart tissue is shown in U.S. Pat. No. 4,705,516 in which an outer orifice ring is sutured to the tissue annulus and an inner orifice ring is then screwed into the outer orifice ring. However, the rings are not locked together and may become unscrewed after extended use.

Implantable heart valves can require fasteners to hold them securely to surrounding tissue in the body. Suturing has been used. However, the use of suturing is time consuming and increases the duration of the implantation surgical procedure. The use of helical fasteners or screws is disclosed in the above cited pending application. However, access one at a time to the multiple helical fasteners used with an implant can be difficult and time consuming. The fasteners face in different directions and a simple tool must be positioned multiple times to approach the implantable heart valve component from several difficult angles around the heart, some of which may be obstructed by adjoining tissue. There is a need for an improved technology for screwing helical fasteners through a heart valve component into a tissue annulus of the heart.

SUMMARY OF THE INVENTION

A bioprosthetic heart valve includes an inner bioprosthetic valve and an outer frame configured to attach to a tissue annulus of a heart. The inner bioprosthetic valve has an exterior shape which substantially matches an interior shape of the outer frame. The exterior shape of the inner valve mates in substantial alignment with the interior shape of the outer frame. An outer frame-inner valve attachment mechanism is configured to couple the inner valve to the outer frame.

DETAILED DESCRIPTION OF THE PREFERRED EMBODIMENTS

Figure 1:
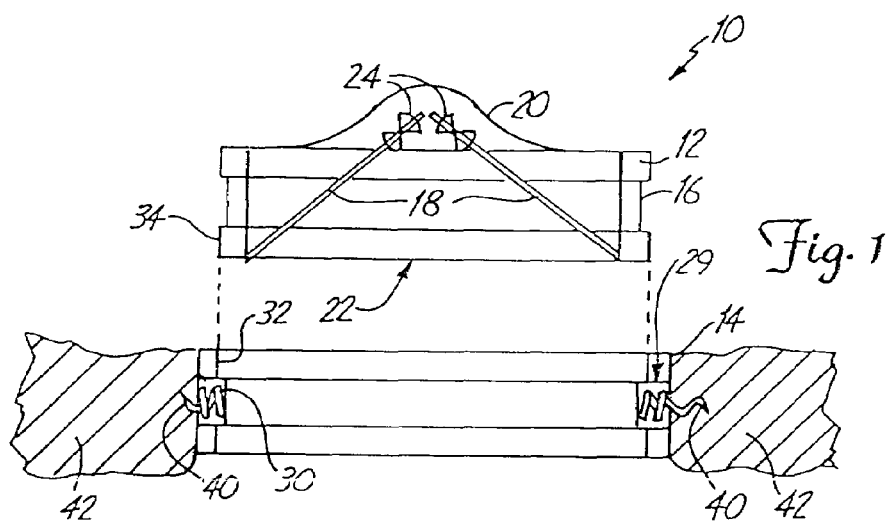
FIG. 1 is an exploded cross-sectional view of a prosthetic heart valve.
Figure 2:
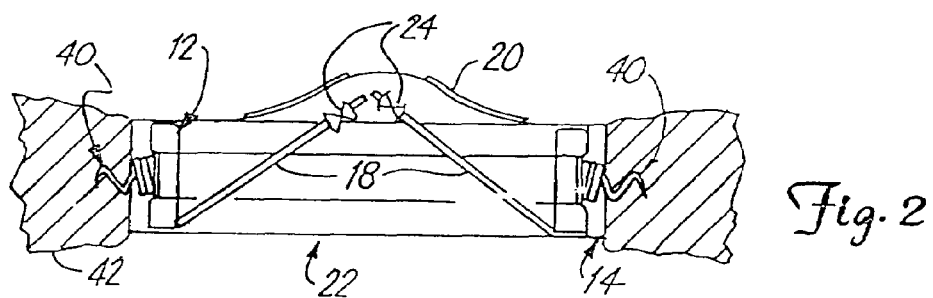
FIG. 2 is a cross-sectional view of the heart valve of FIG. 1.

Heart valve prosthesis 10 shown in FIG. 1 includes inner orifice ring 12 and outer orifice ring 14. FIG. 1 is a side cross-sectional exploded view of valve 10 and FIG. 2 is a side assembled cross-sectional view of valve 10.

Inner orifice ring 12 includes locking recess 16 (or, in another embodiment, a ridge) formed around its outer circumference. Leaflets (or occluders) 18 provide an occluding mechanism and are pivotably coupled to ring 12 at pivot guard 20. Leaflets or occluders 18 move between an open position (not shown) and a closed position as shown in FIGS. 1 and 2 in which flow of fluid through lumen 22 is blocked. Leaflets 18 rotate within pivots 24 formed in pivot guards 20. In one preferred embodiment, inner ring 12 comprises a prosthetic heart valve available from St. Jude Medical, Inc. of St. Paul, Minn., without a sewing cuff carried thereon. However, in some embodiments it may be preferable to use a specially designed inner ring 12.

Outer orifice ring 14 includes locking ridge 30 (or, in another embodiment, a recess) formed on an inner annulus circumference thereon. Inner annulus 32 of ring 14 is sized to have approximately the same radius as outer annulus 34 of inner ring 12. Similarly, locking ridge 30 of outer ring 14 substantially conforms to locking recess 16 of inner ring 12. Locking recess 16 and locking ridge 30 cooperate to provide a ring coupling mechanism adapted to couple the outer orifice ring to the inner orifice ring. Outer orifice ring 14 also includes tissue annulus attachment locking mechanism 40 which, in one preferred embodiment, comprises helical screws carried through holes 29 around the circumference of outer ring 14. Other types of attachment mechanisms include staples, pins, rivets, "nails", barbs, hooks, etc. These mechanisms could be coupled to or integral with the outer orifice ring. As illustrated in FIGS. 1 and 2, locking mechanism 40 attaches to the natural heart tissue annulus 42 of the patient.

Figure 3:
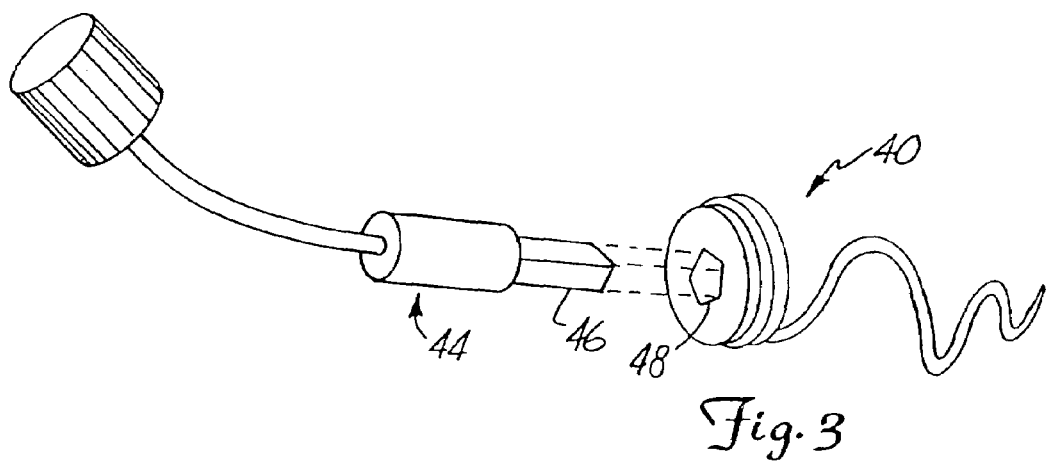
FIG. 3 is a perspective view of an attachment mechanism for the prosthetic heart valve of FIGS. 1 and 2.

In FIG. 3 a perspective view of locking mechanism 40 is shown in greater detail. Locking mechanism 40 is a helical screw preferably made of a biocompatible material. For example, locking mechanism 40 may be formed from a platinum-iridium alloy, MP35N (a Wrought cobalt-nickel-chromium-molybdenum alloy), stainless steel, titanium or other biocompatible materials. As shown in FIG. 3, tool 44 includes engaging tip 46 which fits into screw head 48. Locking mechanism 40 may be turned by rotating tool 44. In one embodiment, there are between 8 and 16 substantially equally spaced locking mechanisms 40 around the circumference of inner orifice ring 12. However, any number may be used. Locking mechanism 40 typically extends between about 0.050 to about 0.200 inches into the tissue annulus 42.

Figure 4:
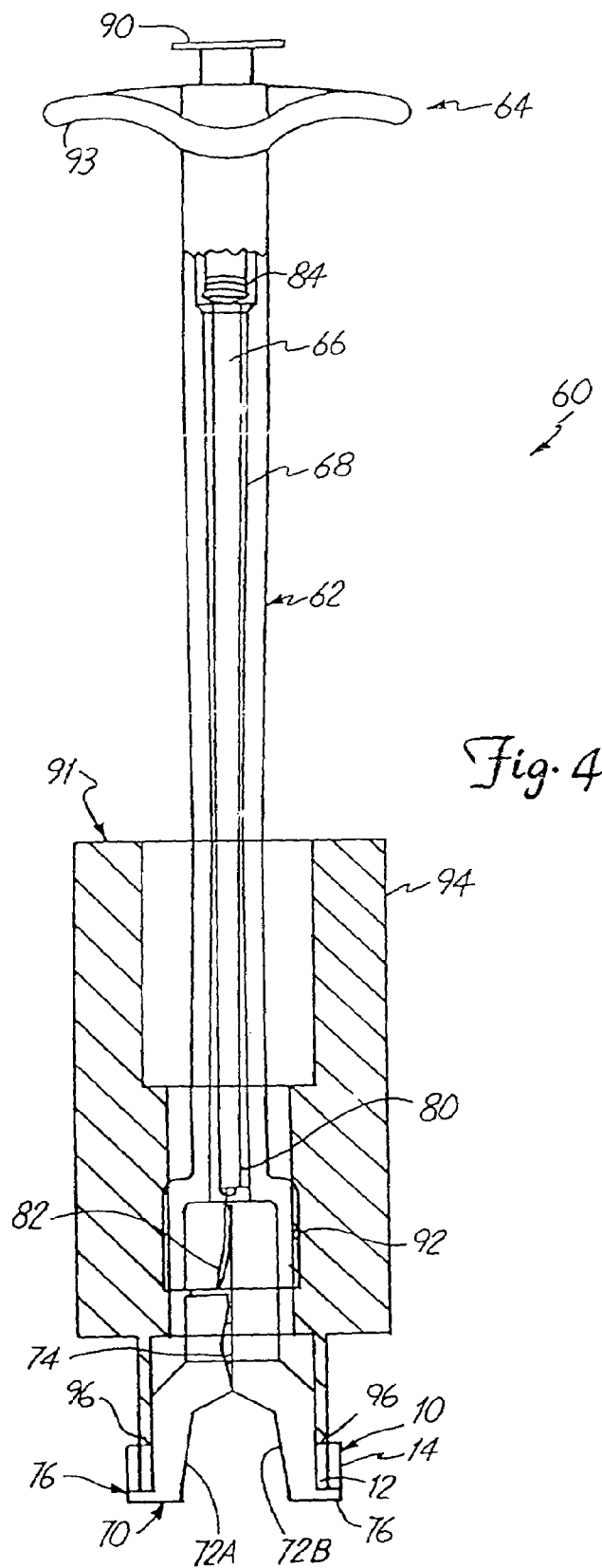
FIG. 4 is a side cross-sectional view of an implantation tool for implanting the heart valve prosthesis shown in FIGS. 1 and 2.

FIG. 4 is a side cross-sectional view of tool 60 for use in snapping inner ring 12 into outer ring 14 of heart valve prosthesis 10 shown in FIGS. 1 and 2. Tool 60 includes elongated handle 62 including proximal gripping end 64. Actuator rod 66 extends through a center opening 68 in handle 62. Holder 70 is coupled to a distal end of handle 62. Holder 70 includes moveable half 72A and fixed half 72B coupled at pivot 74. Halves 72 include lower lip 76 adapted to abut outer ring 14. Distal end 80 of actuator rod 66 couples to actuator cable 82 which is connected to half 72A. Spring 84 is coupled to actuator rod 66 and pushes actuator rod 66 in an axial direction away from holder 70 holding halves 72 in the closed position as shown in FIG. 4. Rod 66 includes actuator button 90. Proximal end 64 of handle 62 includes handle grip 93.

Orifice pushing mechanism 91 is aligned axially with handle 62 and coupled to handle 62 by threads 92. Mechanism 91 includes gripping portion 94 and orifice abutting surface 96. As shown in FIG. 4, orifice abutting surface 96 is adapted to abut inner orifice ring 12.

Figure 5:
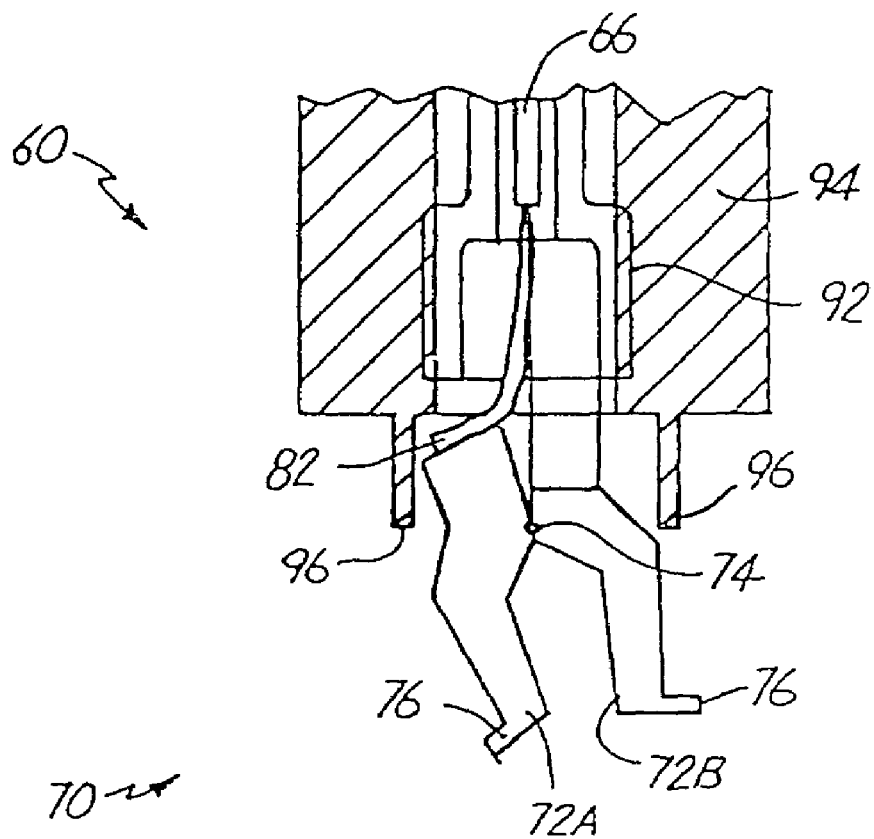
FIG. 5 is a side cross-sectional view of the tool of FIG. 4 in which a holder portion of the tool is moved to an open position.

FIG. 5 is a side cross-sectional view of a portion of tool 60 showing holder 70 in an open position in which half 72A is rotated about pivot 74. In this position, heart valve prosthesis 10 is freed from holder 70 such that heart valve prosthesis may be selectively removed from, or engaged with holder 70.

In operation, pressure is applied to actuation button 90 while grasping handle grip 93. This causes actuator rod 66 to move downward, towards the distal end of tool 60 whereby cable 82 causes half 72A to rotate about pivot 74. When pressure is released from actuator button 90, spring 84 pushes actuator rod 66 in a direction away from holder 70 such that half 72A is moved back into a closed position by cable 82 as shown in FIG. 4. After outer orifice ring 14 has been attached to the natural tissue annulus of the patient's heart, tool 60 containing pre-loaded ring 12 is inserted through implantable ring 14 by depressing actuator button 90. This engages lip 76 under ring 14. Mechanism 94 is then rotated whereby lip 76 and surface 96 work in opposing directions such that no axial force is applied to helical screws 40 or the patient's tissue annulus. Outer orifice ring 14 is held against lower lip 76 such that a relative pressure is applied between rings 12 and 14. This causes locking ridge 30 to seat within locking recess 16. When inner ring 12 has been "snapped" in place with ring 14, ring 12 prevents locking mechanisms 40 from unscrewing or disengaging. Force may then be applied to actuator button 90 such that half 72A of holder 70 rotates as shown in FIG. 5 so that tool 60 may be removed from prosthesis 10.

Figure 6:
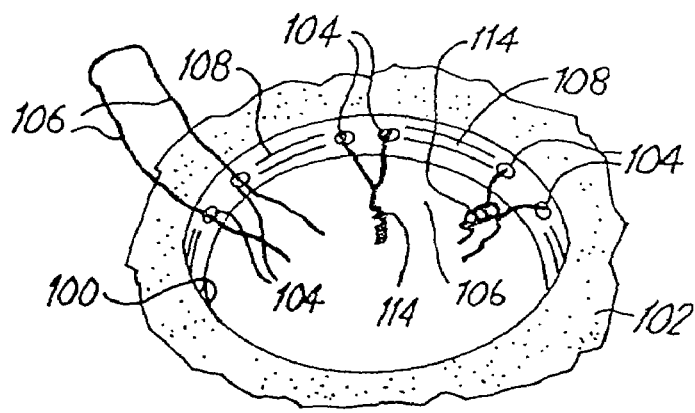
FIG. 6 is a side perspective view of an outer orifice ring in accordance with another embodiment.
Figure 7A:
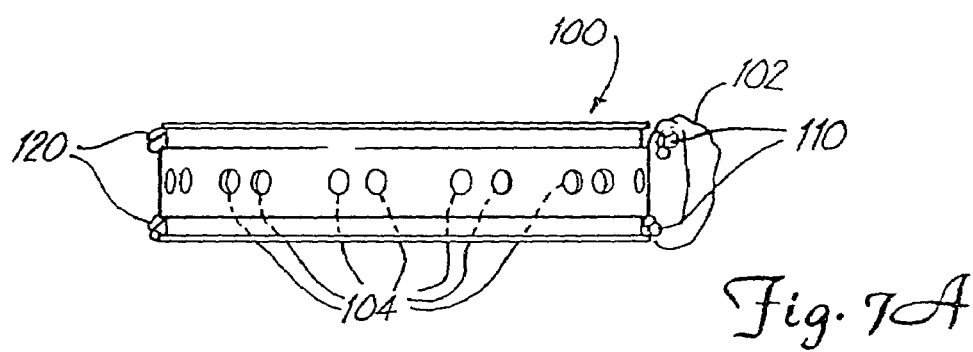
FIG. 7A is a side plan view and FIG. 7B is a side cross-sectional view of the outer orifice ring shown in FIG. 6.
Figure 7B:
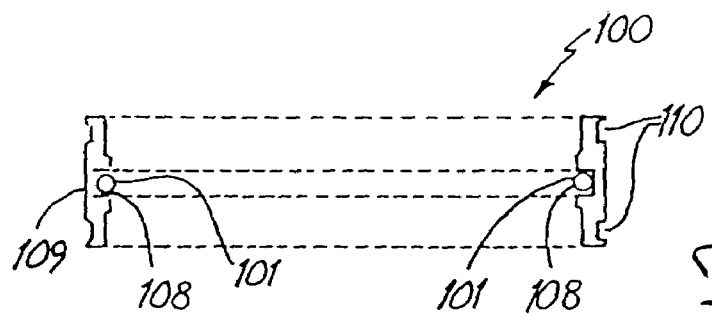

FIG. 6 is a perspective view of outer orifice ring 100 in accordance with another embodiment which is coupled to suture cuff 102. In the embodiment of FIG. 6, ring 100 includes a plurality of suture holes 104 formed therein for receiving sutures 106. Further, the inner annulus of ring 100 includes suture receiving groove 108. FIG. 7A is a side plan view of outer ring 100 and FIG. 7B is a side cross-sectional view of outer ring 100. As shown in FIG. 7A, the outer annulus of ring 100 includes cuff retaining grooves 110 formed therein. In one preferred embodiment, O-rings 101 are provided to prevent leakage between the orifice rings as shown in FIG. 7B. Retaining sutures are wound circumferentially through cuff 102 and within cuff retaining grooves 110 binding or clamping cuff 102 to ring 100.

Ring 100 is sutured to tissue annulus 42 using sutures 106 which extend radially through cuff 102 and suture holes 104. Preferably, sutures 106 are metal sutures of a biocompatible material such as stainless steel. After the sutures 106 are threaded through the patient's natural tissue annulus and outer orifice ring 100, the surgeon secures the suture using knots 114 which may be formed by twisting the suture 106 as shown in FIG. 6. Excess suture material is then trimmed and knots 114 are folded into suture grooves 108.

Figure 8:
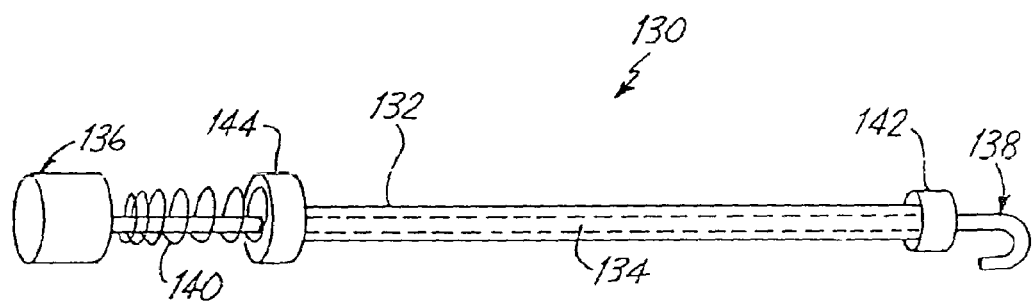
FIG. 8 is a side perspective view of a suture securing tool.

FIG. 8 is a side perspective view of a suture securing tool 130 for use in twisting sutures 106 shown in FIG. 6. Tool 130 includes elongated body 132 carrying shaft 134 therethrough between an actuator 136 and a hook 138. Spring 140 pushes on end cap 144 and body 132 such that hook 138 presses against end cap 142. By pressing on actuator 136, hook 138 may be extended to hook both ends of suture 106. When actuator 136 is released, suture 106 is trapped between hook 138 and cap 142. Tool 130 is then rotated to twist sutures 106 together forming twisted knots 114 shown in FIG. 6.

Following implantation of ring 100 into the tissue annulus 42, inner orifice ring 12 as shown in FIG. 1 is coupled to ring 100 as described with respect to FIGS. 1-5.

Figure 9:
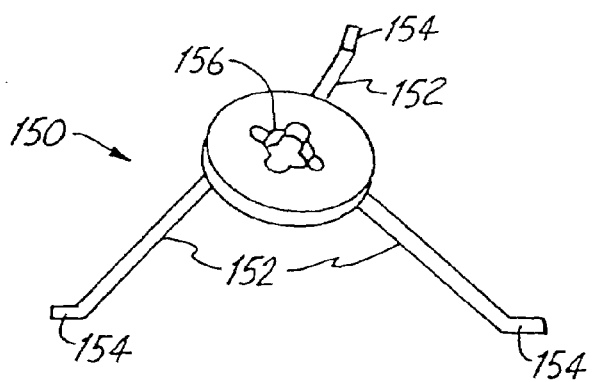
FIG. 9 is a perspective view of a holder for use in implanting an outer ring of a heart valve.

FIG. 9 is a perspective view of implantation tool 150 for use in implanting orifice ring 100. Tool 150 includes legs 152 having coupling tips 154 which are configured to couple to ring 100. Tool 150 may be used by the surgeon to hold ring 100 during suturing such that force may be applied to ring 100. Tips 154 may be fit into suturing grooves 108. Tool 150 includes handle attachment opening 156 which may be used to selectively engage an elongated handle (not shown). Opening 156 can be as shown or can be a threaded hole, a snap fit hole or other opening adapted to selectively engage an elongated handle.

Figure 10:
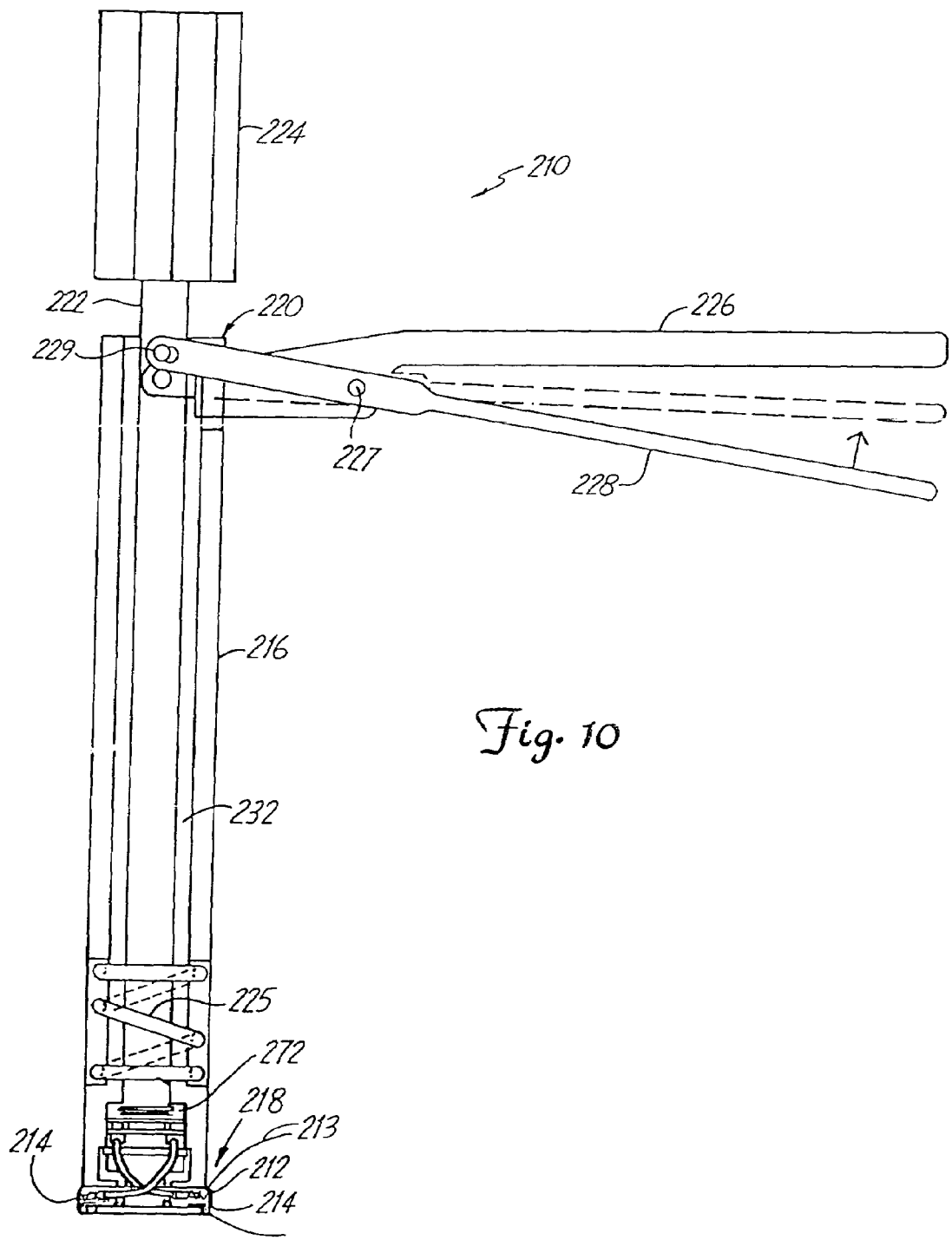
FIG. 10 is a side cross sectional view of a driver tool engaging a heart valve outer ring and coupled to helical fasteners in accordance with the present invention.

In FIG. 10, driver tool 210 is shown engaging outer ring 212 of a two piece prosthetic heart valve. Driver tool 210 couples to helical screw fasteners 214 which pass through holes in outer ring 212. Helical fasteners 214 can be any fastener that advances along its central axis by being turned about that axis, i.e., anything that goes in by twisting, such as a screw. Helical screw fasteners 214 attach outer ring 212 to tissue annulus 213 during an implantation procedure using driver tool 210. Driver tool 210 includes tool housing 216, which is generally cylindrical in shape, or round in cross section, and extends from distal end 218, which engages outer ring 212, to proximal end 220 spaced away from the distal end 218. Drive shaft 222 at proximal end 220 has a handle 224 that can receive a twisting or driving force for transmission to helical screw fasteners 214. Handle 224 can also be actuated or pulled away from the proximal end 220 to disengage driver tool 210 from helical screw fasteners 214.

In FIG. 10, handles 226, 228 project laterally from proximal end 220. Handles 226, 228 can be manually squeezed together to retract or disengage driver tool 210 from outer ring 212. When handles 226, 228 are squeezed together, tool housing 216 slides relative to tube 232. Handles 226, 228 pivot on pin 227. Handle 226 is rigidly coupled to tube 232. Handle 228 has slot 229 engaging a pin in tool housing 216. When handles 226, 228 are squeezed together, tool housing 216 moves toward outer ring 212 while other parts of drive tool 210 remain stationary relative to handle 226. Tool housing 216 pushes outer ring 212 away from tool 210, releasing outer ring 212 from tool 210 when handles 226, 228 are squeezed together. Spring 225 maintains handles 226 and 228 in the open or spread apart position and prevents accidental dislodgement of ring 212.

As an alternative to the handles 226, 228 of FIG. 10, a release button, along with additional springs can be disposed on the proximal end of tool 210. With this alternative, when the installation of helical fasteners 214 is complete, the release button can be pressed, releasing a catch to retract driver tool 210 from outer ring 212.

Figure 11:
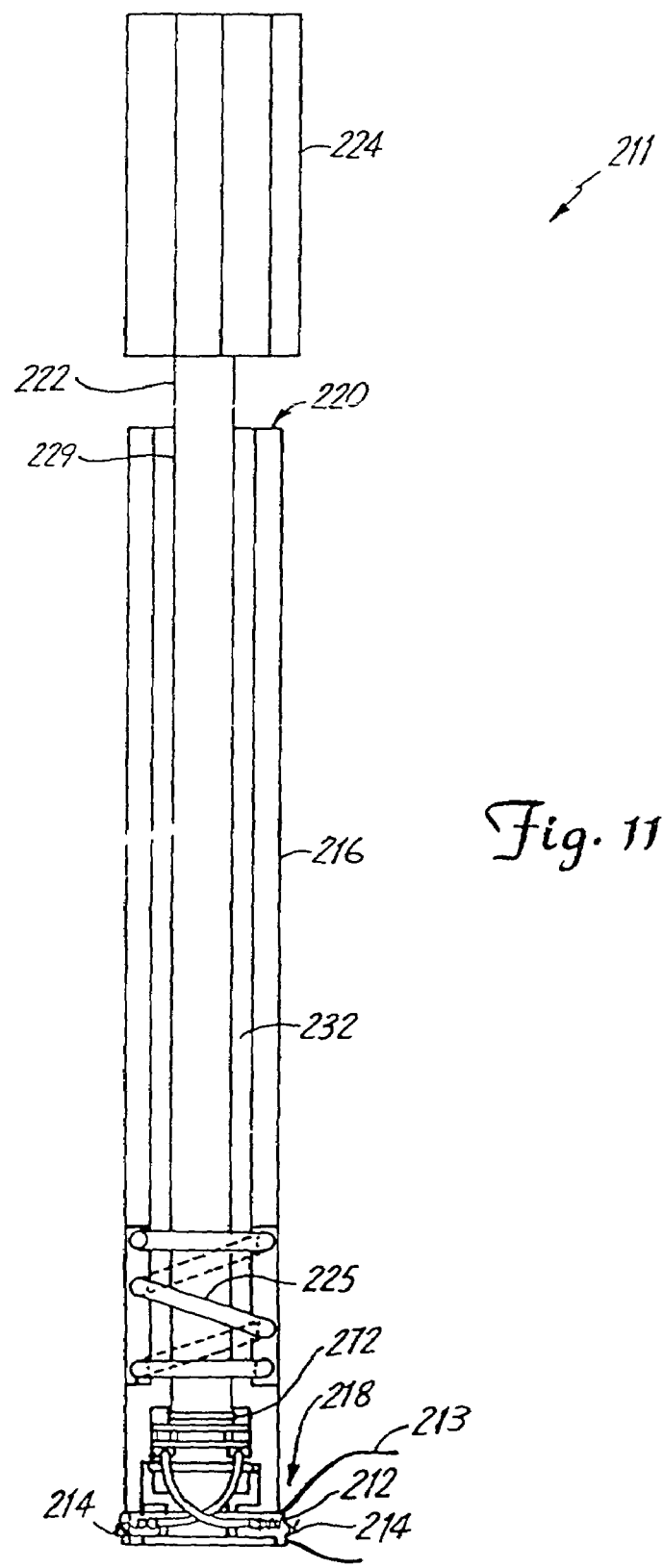
FIG. 11 is a side cross sectional view of a driver tool engaging a heart valve outer ring and coupled to helical fasteners in accordance with the present invention.

In FIG. 11, another alternative embodiment of a tool 211 is shown where there are no handles 226 and 228 as in FIG. 10, and spring 225 prevents accidental dislodgement of ring 212 while the health professional grasps tool housing 216. In FIG. 11, components which are similar to those in FIG. 10 are identified with the same reference numerals used in connection with the description of FIG. 10.

In FIG. 11, after helical screw fasteners 214 are driven in by tool 211 in the same manner that helical screw fasteners 214 are driven in by tool 210 (FIG. 10), the handle 224 is lifted or pulled up relative to tool housing 216 while the surgeon holds tool housing 216. This lifting action first lifts drive shaft 222, compresses spring 272, thereby disengaging helical screw fasteners 214 from the flexible shafts 262 (FIG. 12) of the tool 211. When spring 272 is fully compressed, lifting force is transferred through the compressed spring 272 to tube 232. When the handle is lifted further, tube 232 lifts relative to tool housing 216, compressing spring 225 while tube 232 remains in contact with outer ring 212. Spring 225 is made stiffer than spring 272 so that the flexible shafts 262 (FIG. 12) disengage from the helical screw fasteners 214 before the tube 232 lifts to release outer ring 212 from tool 211. Tool housing 216 moves toward outer ring 212 while other parts of driver tool 211 retract or move away from outer ring 212. The tool 211 is thus fully disengaged from outer ring 212 and helical screw fasteners 214 after use.

Figure 12:
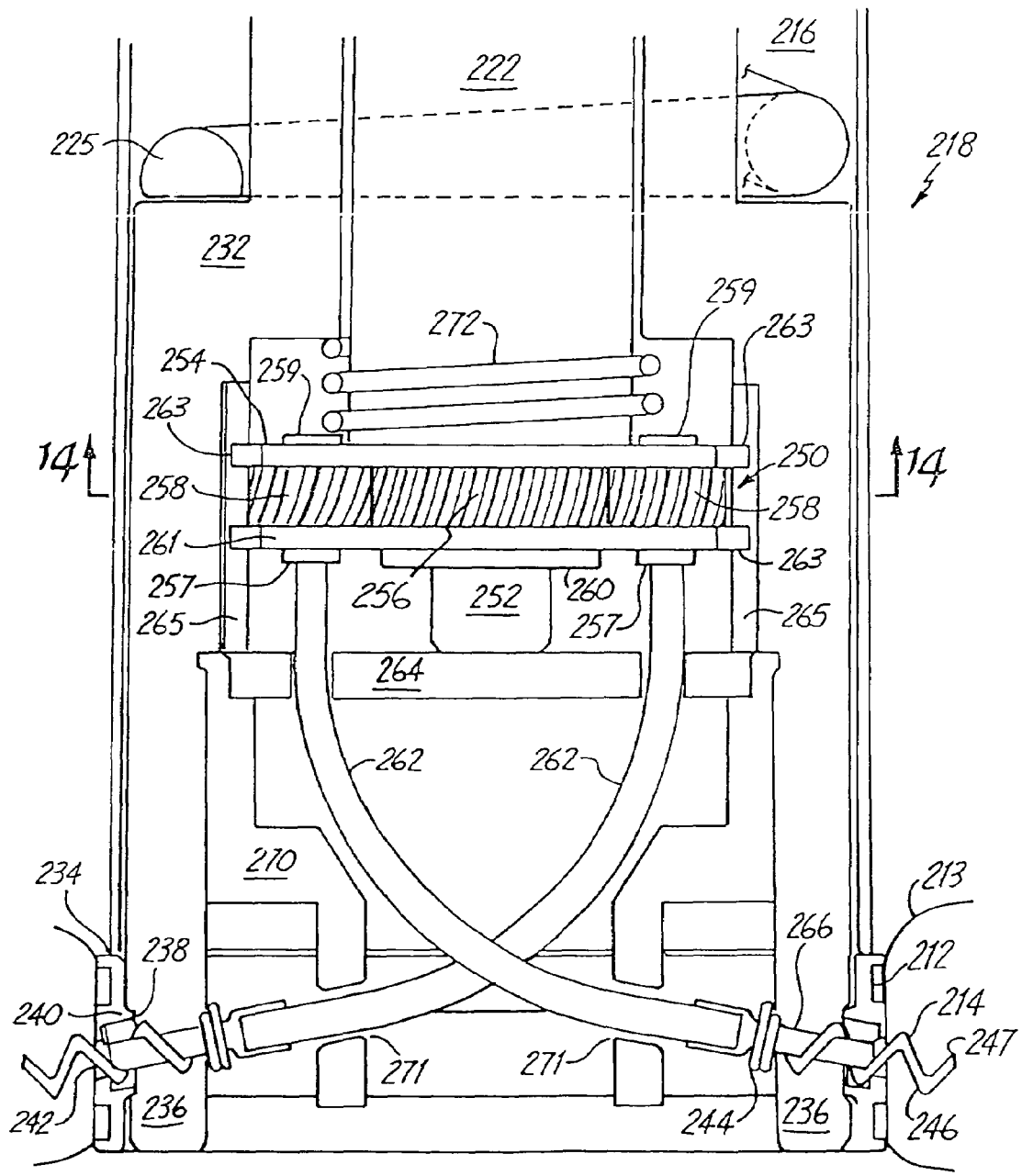
FIG. 12 is an enlarged cross sectional view of the distal end of the driver tool of FIG. 10 or 11.
Figure 19:
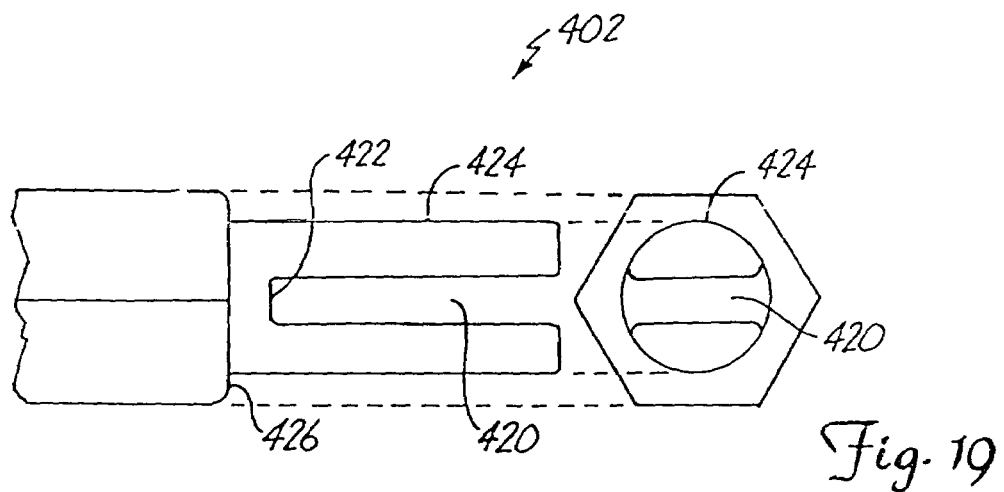
FIG. 19 is an enlarged drawing of a front and an end view of a driver tip for use with the helical screw fastener of FIG. 18.

In FIG. 12, distal end 218 is shown in more detail. At distal end 218, cylindrical end 234 of tool housing 216 abuts outer ring 212. Struts 236 of tube 232 extend beyond cylindrical end 234 to engage outer ring 212 with a snap fit between groove 238 of struts 236 and locking ridge 240 of outer ring 212. Outer ring 212 is thus retained securely on distal end 218. Helical screw fasteners 214 pass through holes 242 in outer ring 212 and into tissue annulus 213. In one embodiment, there are approximately eight to sixteen helical fasteners although any number can be used, each passing through a separate hole 242 in outer ring 212. Helical screw fasteners 214 can be formed of metal wire compatible with implantation, and have a hub portion 244 which is wound in a polygonal shape, typically a hexagon, and the remainder 246 of the helical fastener is wound in a helix with a sharp point 247 at the end. In another embodiment, the last coil of the hub portion 244 turns into the center of the coil (as described later in FIGS. 18-19).

In FIG. 12, drive shaft 222 couples to drive train 250. Drive shaft 222 may be narrowed to form a gear shaft 252 on its end. Gear plate 254 is assembled on gear shaft 252 so that gear shaft 252 is free to spin. Gear 256 is attached to gear shaft 252 so that gear shaft 252 drives gear 256. Satellite gears 258 are assembled on plate 254 with gear hubs 259 extending through holes in plate 254 so that they engage or mesh with gear 256. Plate 261 is also assembled onto gear shaft 252 with gear hubs 257 extending through holes in plate 261 so that gear shaft 252 is free to spin. Retaining ring 260 is then attached to gear shaft 252 to keep gears 256 and satellite gears 258 caged between gear plates 254, 261. Gear plates 254 and 261 are provided with multiple tabs 263 which are shaped to mate with slots 265. This arrangement prevents drive train 250 from rotating within tube 232 when drive shaft 222 is rotated. Satellite gears 258 are coupled to flexible shafts 262 which extend to helical screw fasteners 214. There are multiple satellite gears 258 and multiple flexible shafts 262, however, for clarity only two of each are illustrated in FIG. 12. In one embodiment, if a second gear 256 is provided to drive some of the fasteners. For example, eight shafts 262 could be driven by gear 256 and a second gear (not shown) located above gear 256 could drive eight more shafts 262 which extend vertically through the spaces shown in FIG. 14. Flexible shafts 262 pass through holes in plate 264 and in housing 270. Plate 264 and housing 270 are fixed relative to tube 232 and retain flexible shafts 262 in a favorable orientation to transmit twisting motion from the vertical axis of drive shaft 222 to the axis of each helical screw fastener 214. With the satellite gears 258 held in relatively fixed locations relative to tube 232, when drive shaft 222 is twisted relative to tube 232, gear 256 drives satellite gears 258 so that they distribute twisting motion to all eight, or more, flexible shafts 262 simultaneously. Flexible shafts 262, in turn, couple this twist or drive to the helical screw fasteners 214 (only two are shown in FIG. 12). Driver tips 266 on the ends of flexible shafts 262 are shaped to engage the hub portions 244 of helical screw fasteners 214. Typically, driver tips 266 have a hexagonal, square or cylindrical slotted shape and slidingly engage a correspondingly hexagonal or square or cylindrical slotted hub shape of helical screw fasteners 214 to transmit torque. Torsional drive is thus distributed from drive shaft 222 (or handle 224) through drive train 250 to drive helical screw fasteners 214 into tissue annulus 213. Helical screw fasteners 214 advance at approximately right angles to the hand twisting motion and at approximately right angles to tool housing 216. Driver tool 210 is inserted in a convenient straight direction down the aorta toward the tissue annulus 213, avoiding having to approach individual helical screw fasteners 214 at awkward or difficult angles and at different radial directions. All of helical screw fasteners 214 advance simultaneously, avoiding delay in completing the implantation.

In FIG. 12, cylindrical housing 270 is snap fit in tube 232 and serves as a guide for flexible shafts 262, which reduces binding or tangling of flexible shafts 262. Compression spring 272 presses drive train 250 toward distal end 218 to keep driver tips 266 engaged with helical screw fasteners 214. Handle 224 (FIG. 10) can be pulled away from tool housing 216, compressing spring 272 and moving drive train 250 away from distal end 218. When drive train 250 is moved away from distal end 218, driver tips 266 are slid out of or decoupled from helical screw fasteners 214.

Figure 13:
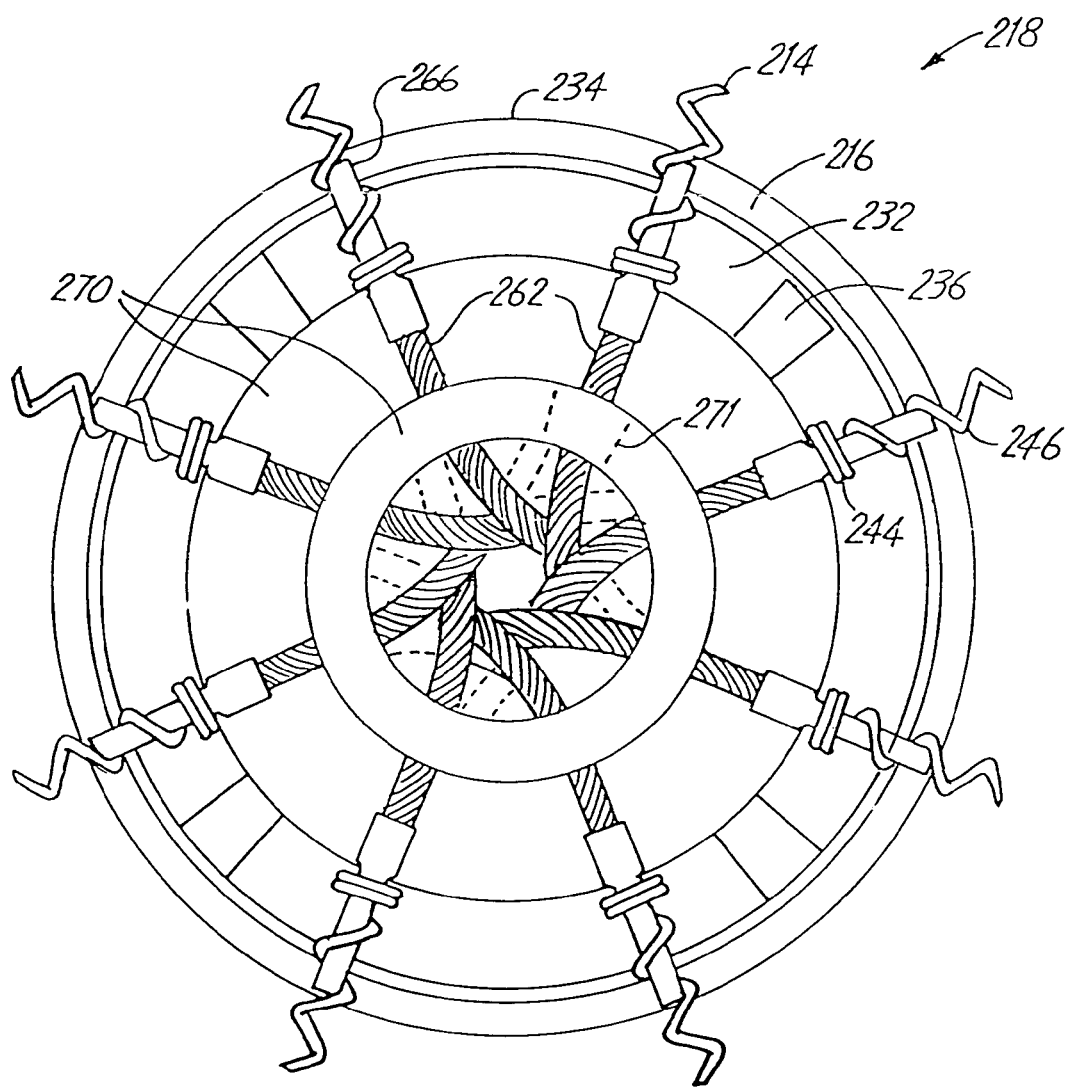
FIG. 13 is an end view of a distal end of the driver tools of FIGS. 10 and 11.

In FIG. 13, an enlarged end view of distal end 218 is shown. In FIG. 13, outer ring 212 has been omitted from the drawing for clarity. End 234 of tool housing 216 is generally cylindrical in shape and houses tube 232 which, in one embodiment, has four struts 236 extending from it. Flexible shafts 262 pass through holes 271 in cylindrical housing 270 and couple with hub portions 244 of helical screw fasteners 214. Helical screw fasteners 214 have a helical portion 246 for engaging tissue. Helical portion 246 also couples with the holes 242 in outer ring 212 (FIG. 12) such that helical screw fasteners 214 are self-advancing when twisted about their central axis. Hub portion 244 of helical screw fasteners 214 slides along driver tips 266 to accommodate the advancing motion. This arrangement keeps the helical screw fasteners 214 retained to the tool 210, preventing the fasteners from becoming prematurely detached from the tool. In one embodiment, shafts 262 extend directly in a radial direction or bend to go to a drive tip 266 at a different location due to space limitations in housing 270. In FIGS. 10-13 all of the helical screw fasteners 214 can be advanced simultaneously into tissue when handle 224 is twisted relative to tool housing 216. Each flexible shaft 262 turns or bends in a different radial direction.

Figure 14:
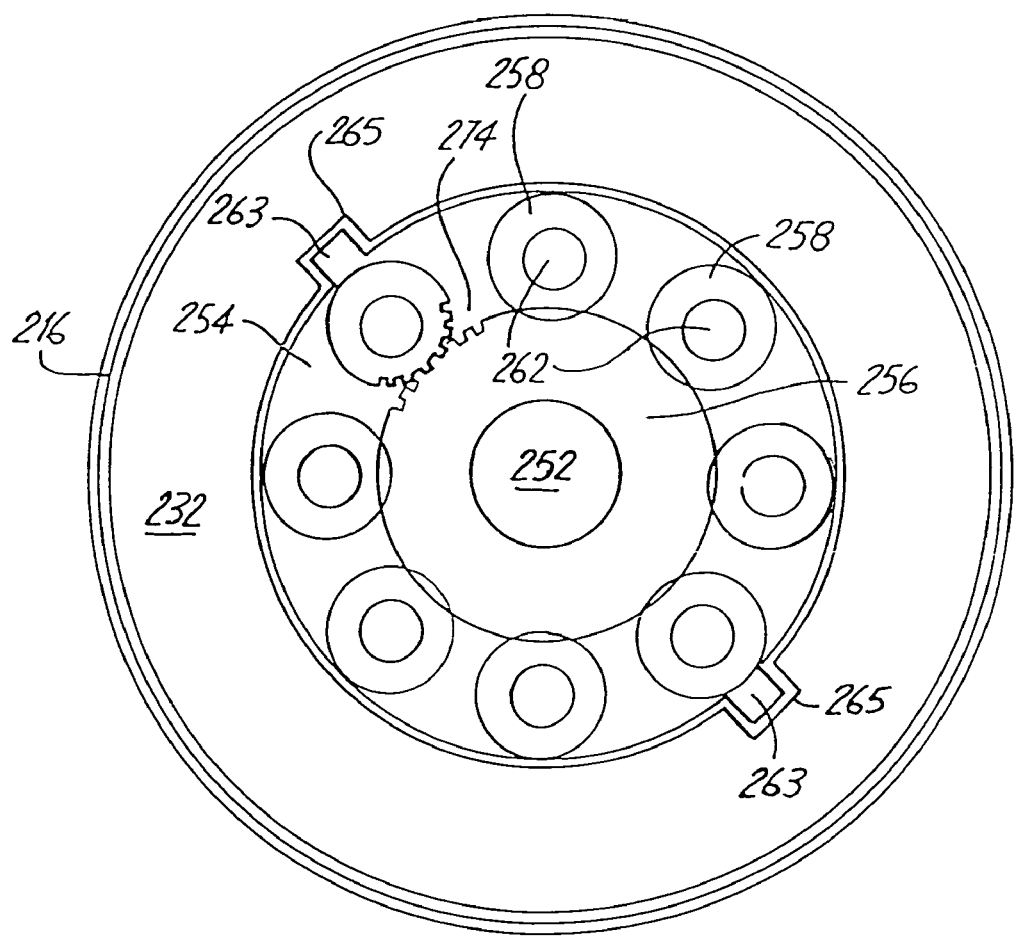
FIG. 14 is a cross sectional view along line 14-14 of FIG. 12.

In FIG. 14, internal construction of drive train 250 is shown. FIG. 14 is a sectional view along line 14-14 of FIG. 12. In this embodiment, gear 256 is shown attached to gear shaft 252 and engaging all (e.g. eight or more) satellite gears 258. Gears 256, 258 are spur gears which mesh with each other as shown only partially at 274. The satellite gears are attached to flexible shafts 262 which serve as axles for the satellite gears 258. Drive train 250 is housed within tube 232 which, in turn, is housed in tool housing 216. The use of flexible shafts permits coupling around sharp, approximately right angle turns with multiple radial directions of drive for the multiple helical fasteners.

The tissue annulus of the heart has been prepared to receive the heart valve prosthesis pursuant to techniques known in the art. Driver tool 210 has been preloaded with outer ring 212 snapped on its distal end 218 and helical screw fasteners 214 inserted in outer ring 212 and coupled to driver tips 266. Distal end 218 is then advanced toward prepared tissue annulus 213 until outer ring 212 is aligned within the tissue annulus. Handle 224 is twisted to advance helical screw fasteners 214 into the tissue annulus. When outer ring 212 is attached by helical screw fasteners 214 to the tissue annulus, handle 224 is lifted relative to tool housing 216. This compresses spring 272 and disengages driver tips 266 from helical screw fasteners 214 if they have not already been disengaged by the advance of the helical fasteners. Handles 226 and 228 are squeezed together, unsnapping outer ring 212 of the heart valve from the tool 210. The tool 210 is removed, leaving outer ring 212 attached to the tissue annulus of the heart by multiple helical fasteners.

Figure 15:
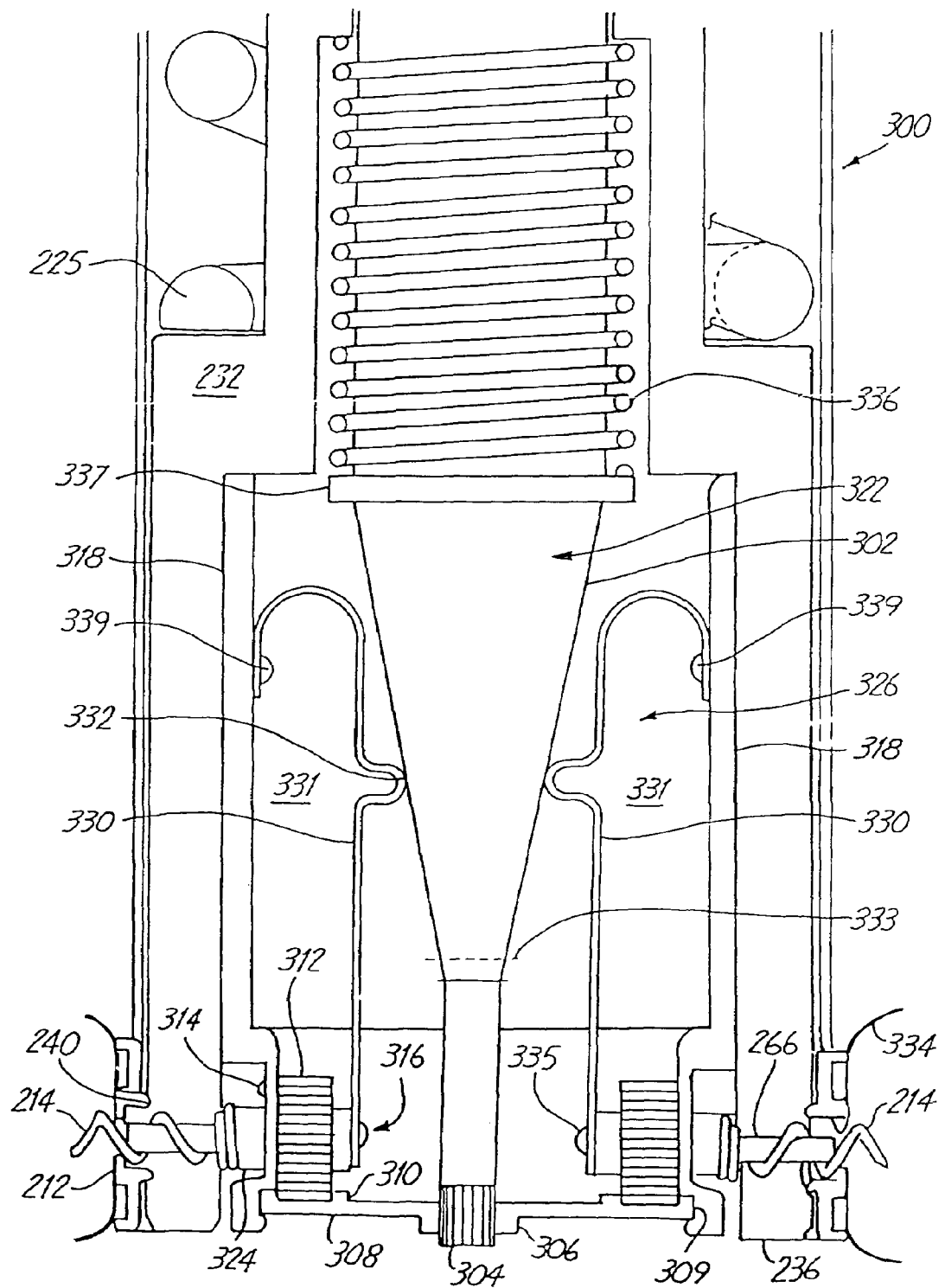
FIG. 15 is an enlarged cross sectional view of an alternate distal end of the driver tools of FIGS. 10 and 11.
Figure 16:
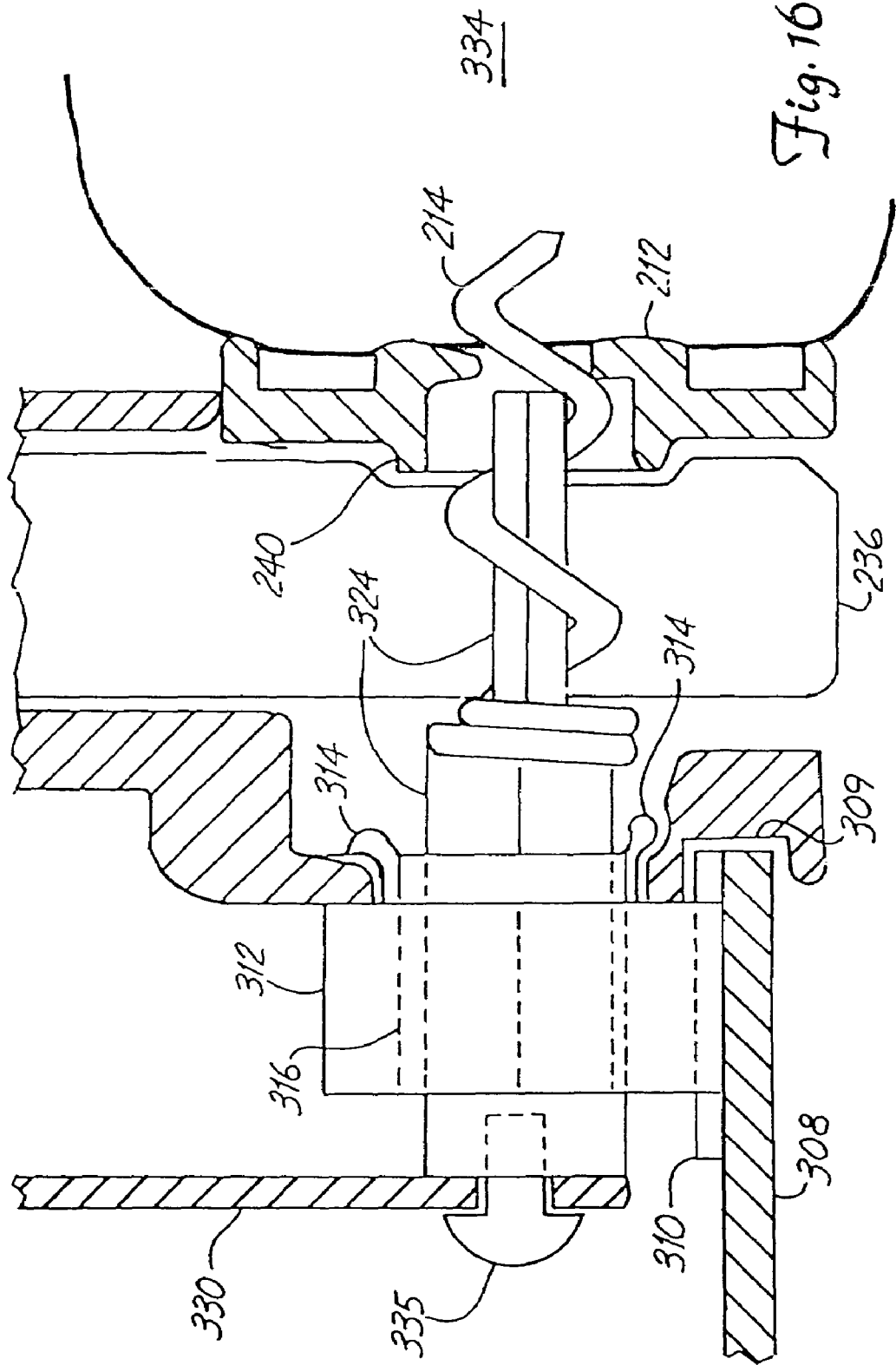
FIG. 16 is a further enlarged cross sectional view of a portion of the alternate distal end of the driver tool of FIG. 15.

In FIGS. 15 and 16, an alternative embodiment 300 of the distal end of the driver tool shown in FIGS. 10 and 11 is shown. In FIG. 15, drive shaft 322, corresponding to drive shaft 222 in FIGS. 10 and 11, has a tapered portion 302 and a splined tip 304 at the distal end. The splined tip 304 engages a central hub 306 of a turntable 308 for rotating the turntable 308. Turntable 308 has a circular gear rack 310 spaced radially outward from the central hub 306. A plurality of spur gears 312 engage the circular gear rack 310 with loose tolerances, allowing for any misalignment between the spur gears 312 and the turntable. Each spur gear 312 has a hub 314 surrounding a throughhole 316 along a central axis of spur gear 312. Each hub 314 is flared or swaged outwardly to secure it to mounting tube 318 such that it is free to spin when driven by circular gear rack 310. Turntable 308 is free to spin in a circular groove 309 formed on the end of mounting tube 318. Each throughhole 316 is shaped to receive and loosely engage a driver tip 324. When driver tips 324 are hexagonal, then throughhole 316 has a corresponding hexagonal shape and is slightly larger than driver tip 324. A spring arrangement 326 coupled to the plurality of driver tips 324 provides axial force to the driver tips 324 for driving helical fasteners 214. Turntable 308 and spur gears 312 comprise a drive train for driving the driver tips 324. Spring arrangement 326 comprises a plurality of springs 330 which can be formed from flat strips of spring steel or other suitable material. Each spring 330 is attached to mounting tube 318 with a fastener 339. Each spring is also attached to a driver tip 324 with a fastener 335 so that driver tip 324 rotates easily on fastener 335 when it is driven by spur gear 312. Each spring 330 engages tapered portion 302 at contact point 332. When drive shaft 322 is down (as illustrated in FIG. 15) the spring arrangement 326 applies a radially outward force to the driver tips assisting with engagement of tissue 334. When drive shaft 322 is lifted up, the contact points 332 engage a narrower cross-section 333 of the tapered portion 302, resulting in a radially inward retraction force on the driver tips 324. Also, when drive shaft 322 is lifted, the turntable 308 disengages from spline 304, allowing the turntable 308 to rotate easily, which facilitates disengagement of driver tips 324. Drive shaft 322 is held in a position for driving by coil spring 336, which is compressed between lip 337 on driveshaft 322 and tube 232. When drive shaft 322 is lifted, spring 336 is compressed first to provide disengagement, and then as drive shaft 322 is lifted further, fully compressed spring 336 transfers lifting force to tube 232, and secondly then, spring 225, which is stiffer than spring 336, is compressed to allow disengagement of struts 236 from protruding ring 240 of outer ring 212.

In the embodiments shown in FIG. 15, the springs 330 can be assisted by additional coil springs secured at location 331, if desired.

Figure 17:
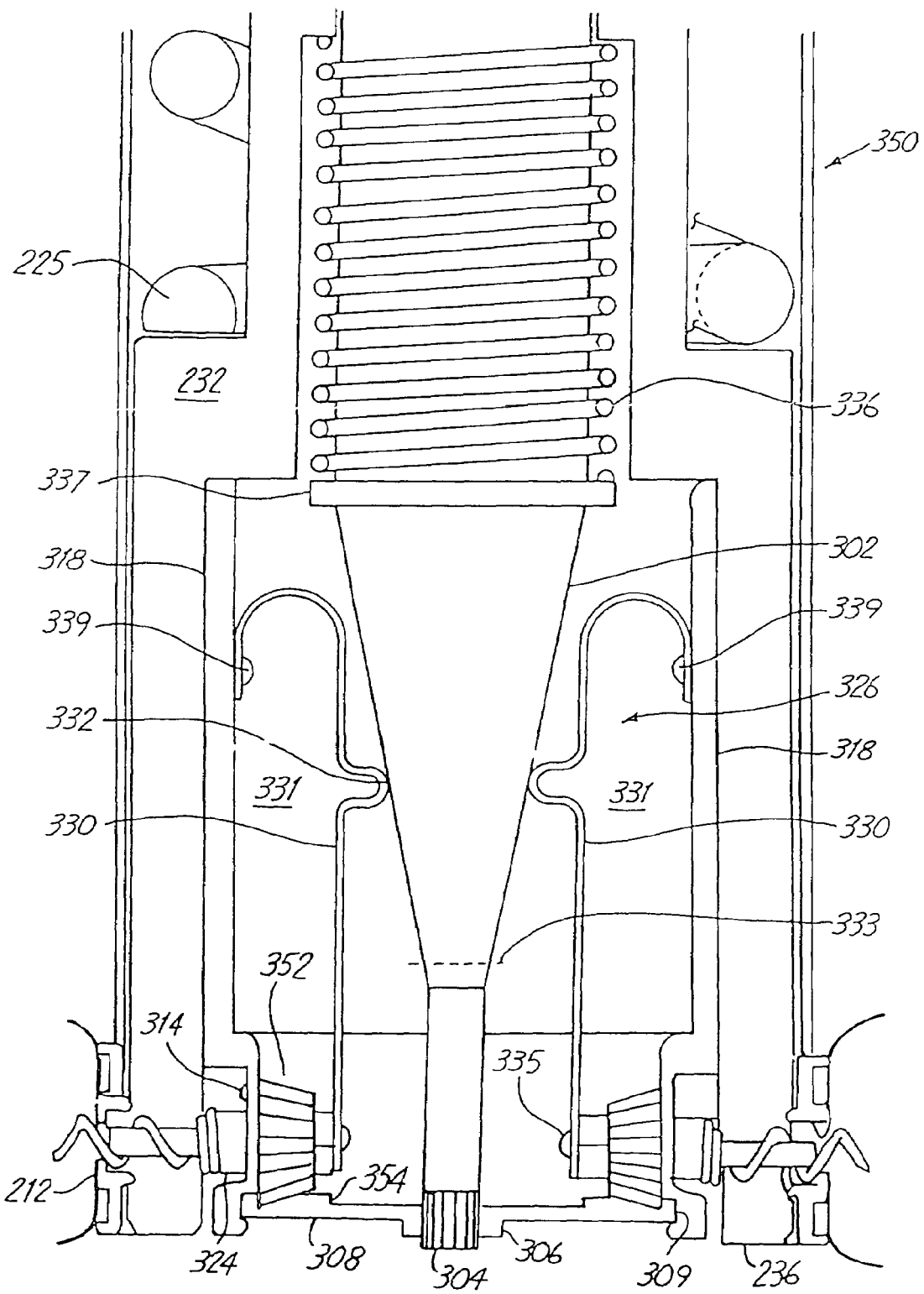
FIG. 17 is an enlarged cross sectional view of an alternate distal end of the driver tools of FIGS. 10 and 11.

In FIG. 17, a further embodiment 350 is shown which is similar to the embodiment shown in FIGS. 15-16, except that the gears 352 are beveled gears and the circular gear rack 354 is correspondingly beveled to engage the beveled gears 352. Parts in FIG. 17 which are similar to those in FIGS. 15-16 have the same reference numbers that are used in FIGS. 15-16.

In the embodiments shown in FIG. 17, the springs 330 can be assisted by additional coil springs secured at location 331, if desired.

Figure 18:
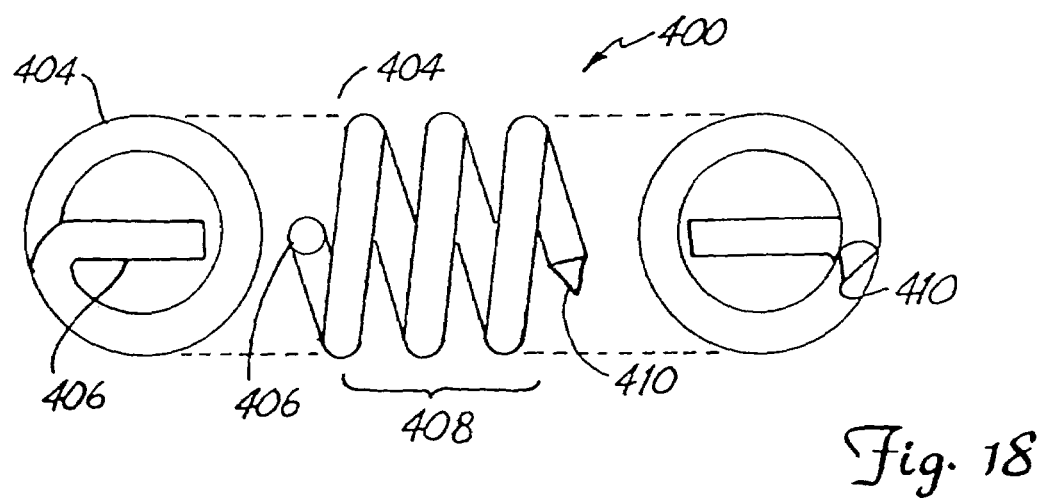
FIG. 18 is an enlarged drawing of front and end views of a helical screw fastener with its last coil turned into the center of the coil.

In FIG. 18, a further preferred embodiment of a helical screw fastener 400 is shown, and a corresponding driver tip 402 is shown in FIG. 1.9. Helical screw fastener 400 has a hub 404 which includes a last coil which turns into the center of helical screw fastener 400 to form a drive lug 406 which can receive a torsional force. Helical screw fastener 400 has a helical main body 408 ending in a sharp point 410 for engaging a tissue annulus such as tissue annulus 213 of FIG. 12. The driver tip 402 of FIG. 19 includes a slot 420 with a slot base 422 for slidingly engaging drive lug 406. The driver tip 402 includes a round shaft 424 which slidingly engages the main body 408 of helical screw fastener 400. The driver tip 402 also includes a shoulder 426 which, along with the slot base 422 provides an axial driving force to helical screw fastener 400, urging the sharp point 410 toward the tissue annulus 213 of FIG. 12. Preferably, helical screws 214 may be coupled with outer ring 212 such that they are self advancing, thereby needing no axial driving force and simply advance into tissue annulus 213 as they are turned. Helical screw fastener 400 and driver tip 402 can be used in the tools shown in FIGS. 10-17.

For convenience, a driver tool 210 as shown in any of FIGS. 10-17, outer ring 212 and multiple helical screw fasteners 214 are provided assembled in a package as a sterilized kit. The tool is preloaded by having outer ring 212 snapped in place on the distal end, helical fasteners preloaded in holes in the outer ring and the driver tips coupled to the helical fasteners.

Preferably, the rings set forth herein are formed of biocompatible materials. The outer ring is generally made of material more flexible than the inner ring, such as polyethylene terephthlate (PET), polyetheretherketones (PEEK), ultrahigh molecular weight polyethylene, Nitinol® (a nickel-titanium alloy), and polyurethane. The inner ring is made preferably of a material more rigid than the outer ring such as titanium, MP35N (wrought cobalt-nickel-chromium-molybdenum alloy), ceramic, Elgiloy® (cobalt-chromium-nickel-molybdenum iron alloy), pyroltic carbon or other rigid polymers for the inner ring. The particular shapes of the orifice rings and attachment mechanisms may be modified as appropriate. The ring coupling mechanism for coupling the two rings may be any mechanism as desired and is not limited to the particular "snap" coupling techniques set forth herein. For example, the coupling techniques may include screws, wires, bayonet locking mechanism, and nails which extend axially and engage the rings. Further, the configuration of the inner orifice ring and its occluding mechanism may be other than those set forth herein.

Implantation time is short and relatively simple implantation techniques can be used. Further, the angular positioning of the leaflets in the inner ring is easily accomplished by rotating the inner ring with respect to the outer ring. The invention allows surgical access to subvalvular features prior to coupling the inner ring to the outer ring without the possibility of damaging the occluding mechanism, for example. The inner valve ring can be removed and replaced without excising the entire prosthesis. The complexity of surgery is reduced because manual suturing may not be required. The area of the lumen is increased over typical prior art designs and a lower profile results because the cuff attachment mechanism requires less area. With the inner ring coupled to the outer ring, the outer ring attachment mechanisms are prevented from "backing out" and completely shielded from blood flow where they could otherwise initiate formation of thrombus. Any type of occluding mechanism may be used and the attachment mechanism may be integral with the ring body. The invention also eliminates suturing such that the implantation procedure is faster. Further, there are no suture tails which could lead to thrombus formation. The invention is also useful in minimally invasive surgery because the attachment is with a single elongate tool which can be placed through a trocar in the patient and the entire valve attached in a single step.

The component parts of tools depicted in FIGS. 10-17 can be constructed of biocompatible polymers such as polyurethane, delrin, polysulfone, of metals such as stainless steel, or of other biocompatible materials. Gears are preferably constructed of nylon, teflon or stainless steel. The completed tool or kit can be gamma sterilized and disposable, if desired. Flexible shafts can be formed of stainless steel and coated with nylon or teflon for lubricity. Helical screw fasteners can be made of platinum-iridium alloy, MP35N (a wrought cobalt-nickel-chromium-molybdenum alloy), stainless steel, titanium or other biocompatible materials. If desired, an electric motor can be used to provide the torsional force rather than manually twisting a handle.

Figure 20:
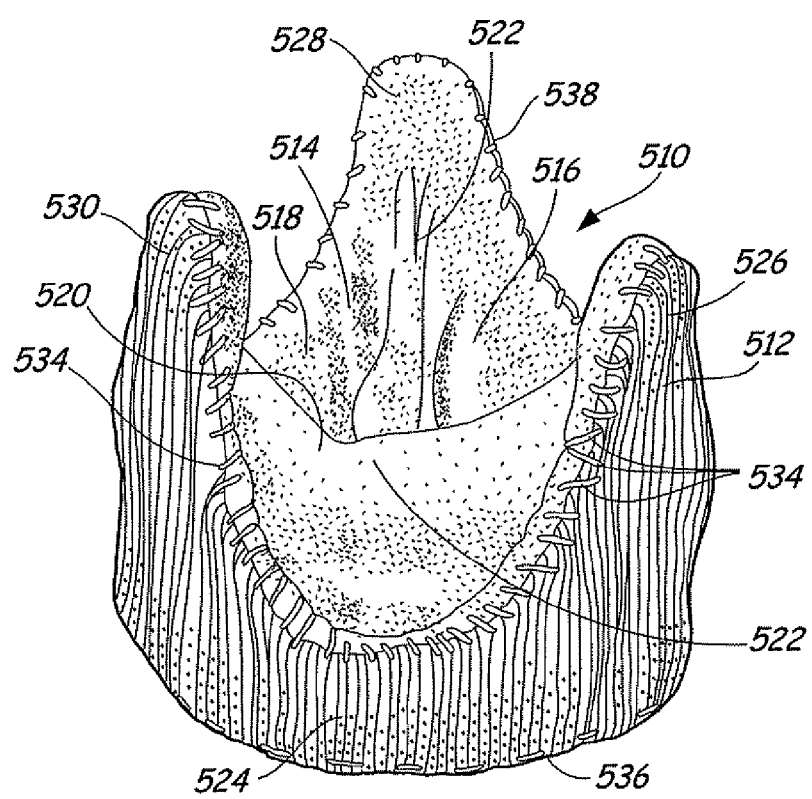
FIG. 20 is a perspective view of a bioprosthetic valve.

The present invention is also applicable to stentless bioprosthetic heart valves. FIG. 20 is a perspective view of such a stentless bioprosthetic heart valve 510, such as the Toronto SPV® valve from St. Jude Medical. Valve 510 includes a covering 512 and is adapted for implantation in the aortic position. Valve 510 includes three leaflets 516, 518 and 520 which meet along coaptation surfaces 522. Covering 512 can comprise a flexible or fabric sheath which is contoured to the external surface of the valve 510. In such an embodiment, covering 512 consists of a generally annular base 524 and three axially projecting and circumferentially-spaced commissure supports 526, 528 and 530. Sutures 534 along inflow edge 536 and outflow edge 538 are used to attach covering 512 to valve 510. Covering 512 can be a biocompatible polymer such as polyester or polytetrafluoroethylene (PTFE).

Figure 21:
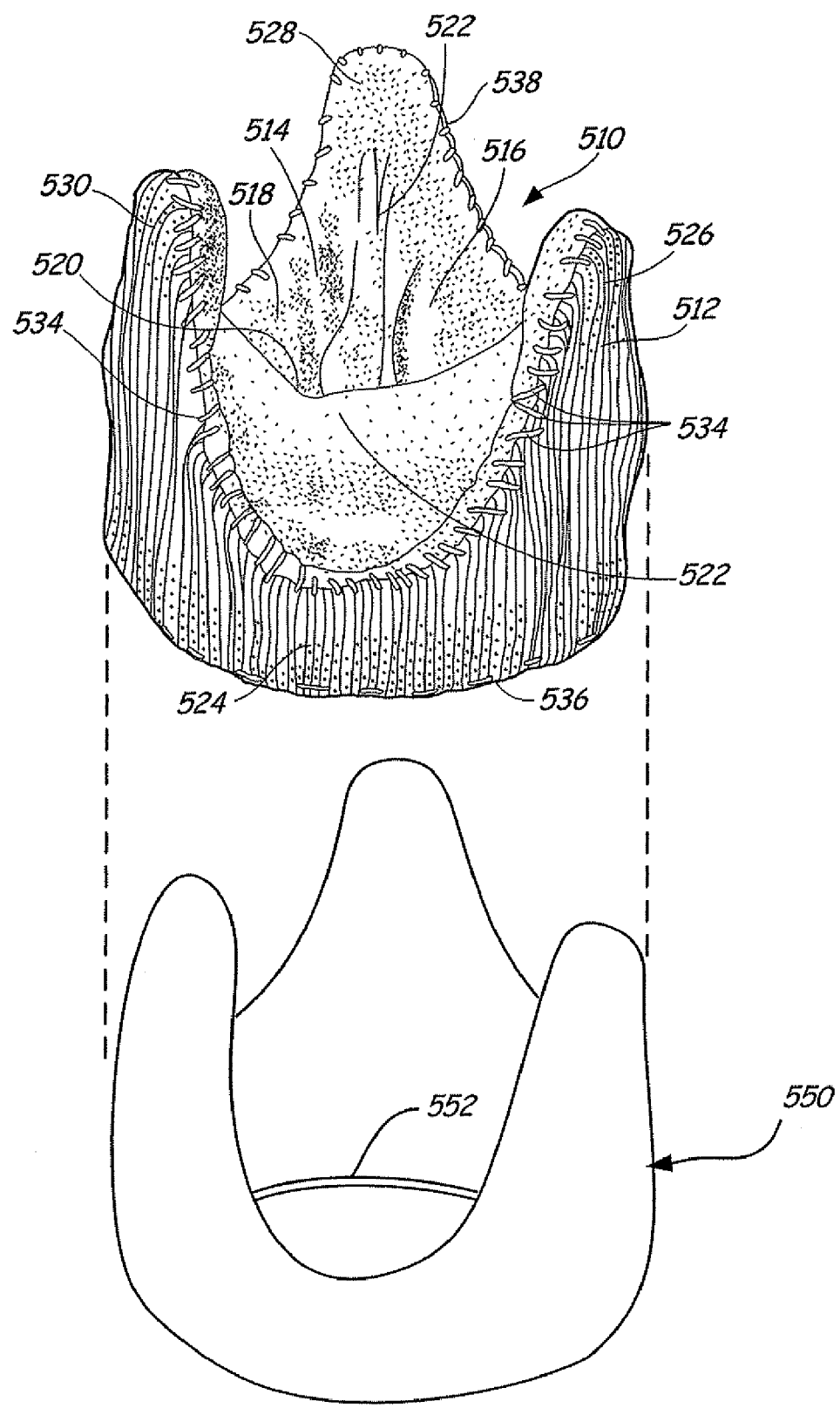
FIG. 21 is an exploded view of the valve of FIG. 20 and an outer frame.

FIG. 21 shows an exploded view of valve 510 and outer frame 550. Outer frame 550 has a shape which substantially matches the outer shape of valve 510 such that valve 510 fits securely within outer frame 550. Outer frame 550 can be secured to the native tissue annulus using any appropriate technique such as sutures, staples or screws, as discussed above, or other techniques. As outer frame 550 does not include the valve structure, it provides improved access to and visibility of the annular and sub-annular regions for the surgeon during the implantation procedure such that the orientation and location of the valve is more accurate. Outer frame 550 is a substantially flexible structure. In one embodiment, it is relatively thin, on the order of about 0.01 to about 0.05 inches (about 0.25 mm to about 1.27 mm), and is made from a flexible biocompatible polymer such as polyester or PTFE in a molded or fabric form. The wall of outer frame 550 can be continuous, meshed, or have perforations.

After outer frame 550 has been implanted, valve 510 is attached to frame 550. This attachment can also be through suturing or other attachment techniques. In one embodiment, an adhesive is used to secure valve 510 to frame 550. One such adhesive is described in U.S. patent application Ser. No. 09/235,138, filed Jan. 22, 1999. For example, a chemically activated adhesive can be used in which the activating chemical is applied to outer frame 550 or valve 510 separately or combined together on either the frame 550 or valve 510 just prior to implantation. If an adhesive is used, a holder can be provided to hold the valve against frame 550 during the adhesion process. Preferably, the holder would have a shape which substantially matches the shape of outer frame 550. Such a holder preferably maintains pressure between the valve 510 and the outer frame 550. For example, the holders can include an inflatable membrane similar to a balloon such that a force can selectively be applied from the valve 510 to the outer frame 550 while the adhesive cures.

These configurations allow the surgeon to use an adhesive without requiring the adhesive itself to be accurately applied to the native tissue during implantation. Further, as the adhesive will be placed on the frame 550 and/or valve 510, the adhesive will not drift into undesirable areas in the internal part of the valve such as the coronary ostia or into the left ventricle. A stronger and more consistent bond can be obtained because the adhesive will bond between similar materials as opposed to trying to bond the valve 510 directly to the native tissue. The invention reduces the time required to implant the valve, provides improved control of adhesive placement and improves bond reliability between similar materials.

A continuous or partial ridge 552 can be provided along the inflow edge of frame 550 to aid in the alignment and placement of valve 510 within frame 550. For example, the inflow edge 536 of valve 510 abuts ridge 552 when valve 510 has been accurately placed, and commissure supports 526, 528, 530 are in vertical alignment with the corresponding features of outer frame 550. Valve 510 can be rotated to the correct alignment before the adhesive cures. During implantation, the inner valve 510 mates in substantial alignment with outer frame 550.

Figure 22:
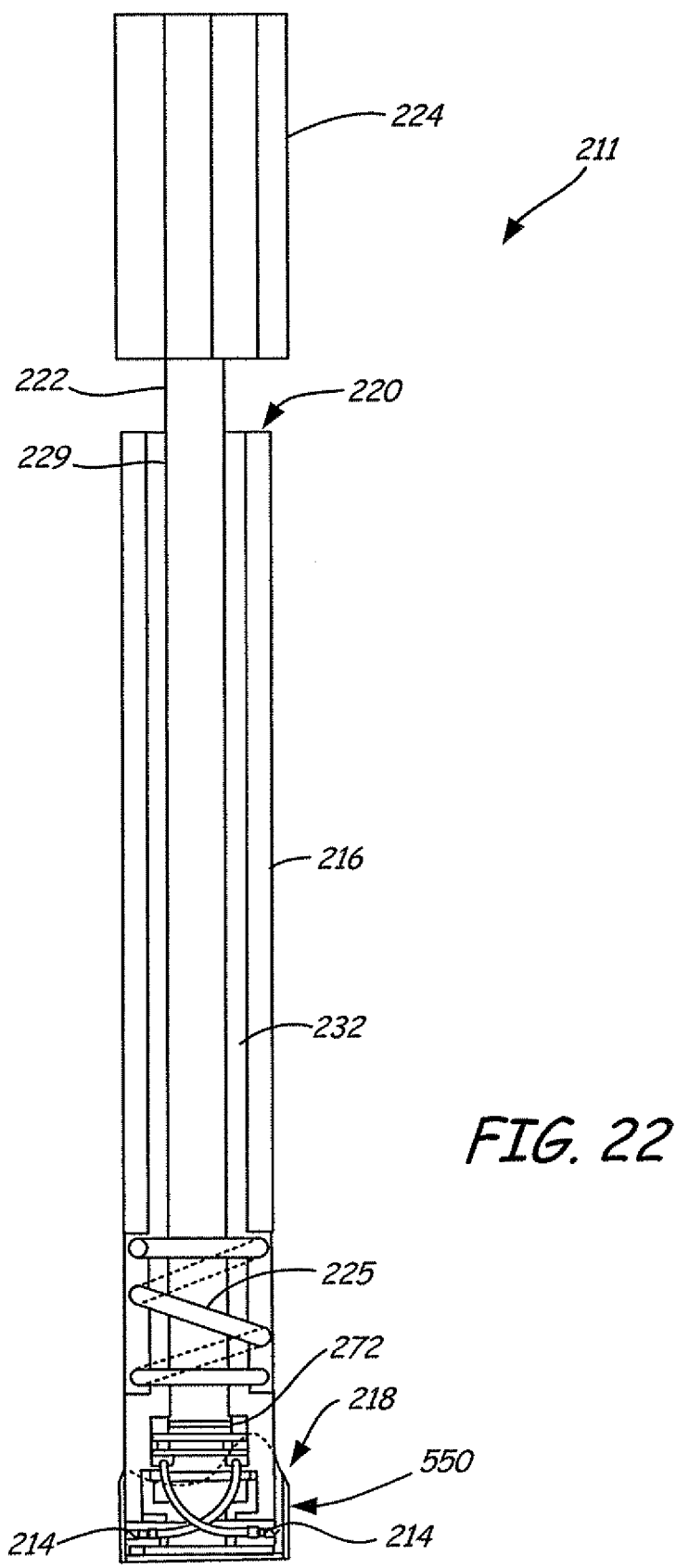
FIG. 22 is a side cross-sectional view of an implantation device and the outer frame of FIG. 21.

The outer frame 550 can be implanted using the techniques set forth herein. For example, FIG. 22 is a side cross sectional view similar to FIG. 11 showing tool 211 carrying outer frame 550 at distal end 218. Screws 214 extend through outer frame 550 and can be used to attach outer frame 550 to the native tissue annulus as discussed above. Although FIG. 22 illustrates screws 214 located in a single plane near the inflow edge of outer frame 550, additional screws can be positioned at other locations on frame 550 to provide improved attachment. In such an embodiment, additional flexible shafts 262 such as those shown in FIG. 12 can be provided to simultaneously actuate additional screws. Once the valve 510 is coupled to outer frame 550, the heads of screws 214 are covered by valve 510 and secured in place. Sutures or staples can also be used to implant outer frame 550. In one aspect, any type of surgical attachment mechanism can be used to implant outer frame 550.

Although the present invention has been described with reference to preferred embodiments, workers skilled in the art will recognize that changes may be made in form and detail without departing from the spirit and scope of the invention.

What is claimed is:

1. A bioprosthetic heart valve, comprising:
    an outer frame configured to attach to a tissue annulus of a heart and having an interior surface and frame posts;
    an outer frame-tissue annulus attachment mechanism comprising a plurality of screws, configured to couple the outer frame to the tissue annulus of the heart;
    an inner bioprosthetic valve having an exterior surface and commissure supports, the exterior surface and commissure supports of the inner valve mating in substantial alignment with the interior surface and frame posts of the outer frame; and
    an outer frame-inner valve attachment mechanism configured to couple the inner valve to the outer frame.

2. The bioprosthetic heart valve of claim 1 wherein the outer frame-inner valve attachment mechanism comprises an adhesive.

3. The bioprosthetic heart valve of claim 1 wherein the outer frame comprises a polymer.

4. The bioprosthetic heart valve of claim 1 wherein the outer frame-inner valve attachment mechanism comprises a suture.

5. The bioprosthetic heart valve of claim 1 wherein the outer frame includes a ridge on the interior surface of the outer frame, and the inner bioprosthetic valve abuts the ridge.

6. The bioprosthetic heart valve of claim 1 wherein the outer frame is flexible.

7. The bioprosthetic heart valve of claim 1 wherein the outer frame comprises a material and the inner valve exterior surface comprises the same material.

8. A bioprosthetic heart valve, comprising:
    an outer frame configured to attach to a tissue annulus of a heart, the outer frame having frame posts and an interior surface which has a substantially cylindrical cross-section and an annular ridge;
    an outer frame-tissue annulus attachment mechanism configured to couple the outer frame to the tissue annulus of the heart, wherein the outer frame-tissue annulus attachment mechanism comprises a plurality of screws;
    an inner bioprosthetic valve having an exterior surface and commissure supports, the inner valve configured to be slidably received in the outer frame when the outer frame is attached to the tissue annulus of the heart, such that the exterior surface of the inner valve abuts the annular ridge and the commissure supports mate in substantial alignment with the frame posts of the outer frame; and
    an outer frame-inner valve attachment mechanism configured to couple the inner valve to the outer frame after the outer frame is attached to the tissue annulus.

9. A bioprosthetic heart valve, comprising:
    an outer frame configured to attach to a tissue annulus of a heart, the outer frame comprising frame posts and an interior surface;
    an inner bioprosthetic valve comprising commissure supports, the commissure supports of the inner valve mating in substantial alignment with the frame posts of the outer frame, the inner valve having an exterior surface;
    an outer frame-inner valve attachment mechanism configured to couple the inner valve to the outer frame after the outer frame is attached to the tissue annulus; and
    an outer frame attachment mechanism configured to couple the outer frame to tissue of the heart, wherein the outer frame attachment mechanism comprises a plurality of screws.

* * * * *